(12) United States Patent
Nishino et al.

(10) Patent No.: US 8,278,632 B2
(45) Date of Patent: *Oct. 2, 2012

(54) VESSEL STERILIZATION APPARATUS

(75) Inventors: Yukinobu Nishino, Kanazawa (JP); Tokuo Nishi, Kanazawa (JP); Yukihiro Yamamoto, Kanazawa (JP)

(73) Assignee: Shibuya Kogyo Co., Ltd., Kanazawa-shi (JP)

( * ) Notice: Subject to any disclaimer, the term of this patent is extended or adjusted under 35 U.S.C. 154(b) by 21 days.

This patent is subject to a terminal disclaimer.

(21) Appl. No.: 12/734,708

(22) PCT Filed: Nov. 10, 2008

(86) PCT No.: PCT/JP2008/070391
§ 371 (c)(1),
(2), (4) Date: May 17, 2010

(87) PCT Pub. No.: WO2009/069455
PCT Pub. Date: Jun. 4, 2009

(65) Prior Publication Data
US 2010/0270477 A1 Oct. 28, 2010

(30) Foreign Application Priority Data

Nov. 30, 2007 (JP) ................................. 2007-310413

(51) Int. Cl.
*A61L 2/08* (2006.01)
*H01J 37/20* (2006.01)
(52) U.S. Cl. ............... 250/491.1; 250/492.1; 250/493.1; 250/455.11; 422/22; 204/157.15
(58) Field of Classification Search ............... 250/491.1, 250/492.1, 493.1, 455.11; 422/22; 204/157.15
See application file for complete search history.

(56) References Cited

U.S. PATENT DOCUMENTS 4,511,027 A 4/1985 Zamboni
(Continued)

FOREIGN PATENT DOCUMENTS

DE 3238332 A1 6/1983
(Continued)

OTHER PUBLICATIONS

PCT/ISA/210 dated Feb. 10, 2009 (4 pages).
(Continued)

*Primary Examiner* — Nikita Wells
(74) *Attorney, Agent, or Firm* — Flynn, Thiel, Boutell & Tanis, P.C.

(57) ABSTRACT

In an irradiation region A in which an electron beam irradiator emits an electron beam through an irradiating surface 12*a* of the electron beam irradiator, a resin bottle 8 is conveyed with a distance between the irradiating surface 12*a* and the resin bottle 8 being maintained constant. Grippers 6 are arranged to an outer peripheral portion of a rotary body 14 in a circumferential direction thereof at an equal interval, and the resin bottles 8 are conveyed with neck portions 8*a* thereof being held. Rotating means (52, 58, 62) for rotating the grippers 6 with respect to the rotary body 14 and forward/rearward moving means (18, 50) keeping constant a distance from the irradiating surface 12*a* of the electron beam irradiator are provided. In the electron beam irradiation region A, the gripper 6 is moved forward or rearward in a radial direction by the forward/rearward moving means in the electron beam irradiation region A to thereby maintain constant the distance between the resin bottle 8 and the electron beam irradiating surface 12*a*.

2 Claims, 6 Drawing Sheets

U.S. PATENT DOCUMENTS

| | | | |
|---|---|---|---|
| 7,145,155 B2 * | 12/2006 | Nablo et al. | 250/492.1 |
| 7,435,981 B2 * | 10/2008 | Naka et al. | 250/492.3 |
| 2007/0018115 A1 | 1/2007 | Naka et al. | |
| 2010/0252752 A1 * | 10/2010 | Nishino et al. | 250/491.1 |
| 2011/0012032 A1 * | 1/2011 | Bufano et al. | 250/492.3 |

FOREIGN PATENT DOCUMENTS

| | | |
|---|---|---|
| EP | 1 736 174 A1 | 12/2006 |
| GB | 2 113 167 A | 8/1983 |
| IT | 1145100 | 11/1986 |
| JP | 58-100010 | 6/1983 |
| JP | 11-137645 | 5/1999 |
| JP | 2006-6726 | 1/2006 |
| JP | 2007-29709 | 2/2007 |

OTHER PUBLICATIONS

PCT/ISA/220 dated Feb. 10, 2009 (4 pages).
PCT/ISA/237 dated Feb. 10, 2009 (4 pages).

* cited by examiner

VESSEL STERILIZATION APPARATUS

TECHNICAL FIELD

The present invention relates to a vessel sterilization apparatus for sterilizing vessels held by a gripper of a rotary-type vessel conveying device by irradiating the vessels with electron beam during conveyance thereof while being rotated.

BACKGROUND TECHNOLOGY

A vessel sterilization apparatus, which sterilizes a vessel conveyed in a state of being held by a gripper of a vessel conveying device by irradiating the vessel with electron beam from an electron beam irradiator, is conventionally known (for example, refer to Patent Document 1). The electron beam irradiator described in this Patent Document 1 is provided with a plurality of vessel holding means (grippers) around a rotary body at an equal interval in a circumferential direction, and the vessels are held by such vessel holding means, respectively, and are rotated and conveyed by the rotation of the rotary body. The electron beam irradiator is arranged along a conveying path so as to irradiate the vessel with the electron beam during the conveyance thereof in the state of being held by the vessel holding means.
Patent Document 1: Japanese Patent Application Laid-open Publication No. 2007-29709

DISCLOSURE OF THE INVENTION

Problems to be Solved by the Invention

In a conventional electron beam sterilization apparatus, an electron beam irradiating surface of the electron beam irradiator emitting the electron beam generally has a flat surface shape more than the structure of the invention disclosed in the above Patent Document 1. On the other hand, in the rotary-type vessel conveying device of the structure mentioned above, the vessel conveying path has a circular-arc shape, and according to the movement of the vessel, a distance between the irradiating surface of the electron beam irradiator and a surface of the vessel to be irradiated changes. As mentioned above, if such distance varies, dose of the electron beam irradiating the vessel varies, leading to non-effective sterilization, thus being not preferred.

If the sterilized vessel which is being conveyed by the rotary-type vessel conveying device has, for example, a rectangular shape, an angle of a surface to be irradiated with the electron beam with respect to the irradiating surface of the electron beam irradiator gradually varies during the movement of the vessel on the circular-arc shaped conveying path, which results in deteriorated irradiation efficiency.

The present invention was conceived to solve the above defect, and an object thereof is to provide a vessel sterilization apparatus capable of maintaining a constant distance between a vessel and an irradiating surface of an electron beam irradiator in an irradiation region in which the vessel is irradiated with the electron beam emitted through the irradiating surface of the electron beam irradiator. Moreover, another object thereof, for example, is to provide a vessel sterilization apparatus capable of maintaining a parallel condition of an angle constituted by the irradiating surface of the electron beam irradiator and the surface of the vessel to be irradiated in the irradiating region in a case of the vessel to be irradiated having a rectangular shape.

Means for Solving the Problem

The present invention includes a gripper arranged in an outer periphery of a rotary body so as to hold a vessel, drive means for rotating the rotary body, electron beam irradiating means having a flat electron beam irradiating surface and irradiating the vessel, conveyed with being held by the gripper, with the electron beam, and forward/rearward moving means for moving the gripper forward or rearward with respect to the irradiating surface, wherein a distance between the irradiating surface and the surface of the vessel to be irradiated is maintained to be substantially constant in an irradiation region in which the electron beam is irradiated through the irradiating surface.

Further, the invention defined in claim 2 is characterized by further including rotating means for rotating the gripper with respect to the rotary body, wherein an area in which the gripper is rotated is formed so that the irradiating surface and the surface to be irradiated to the vessel are opposed in a constant direction in the irradiation region.

Furthermore, the invention defined in claim 3 is characterized in that the gripper is rotated by substantially 180 degrees in the irradiation region.

EFFECTS OF THE INVENTION

According to the vessel sterilization apparatus of the present invention, since the distance between the electron beam irradiating surface and the surface of the vessel to be irradiated is kept substantially constant in the irradiation region in which the electron beam irradiator irradiates the vessel with the electron beam through the irradiating surface, so that the vessel can be effectively irradiated with the electron beam to thereby effectively sterilize the vessel.

EXPLANATION OF REFERENCE NUMERALS

A irradiation region
6 gripper
8 vessel (resin bottle)
12a irradiating surface
14 rotary body
18 forward/rearward moving means (forward/rearward moving rod)
50 forward/rearward moving means (forward/rearward moving cam)

BEST MODE FOR EMBODYING THE INVENTION

The vessel sterilization apparatus includes grippers disposed to peripheral portions of a rotary body rotated and driven by driving means, rotating means for rotating the grippers with respect to the rotary body and an electron beam irradiator having a flat irradiating surface and irradiating vessels conveyed, in a state of being held by the grippers, with an electron beam, and achieves an object of effectively irradiating a surface of the vessel with the electron beam emitted from the irradiating surface by the structure in which a distance between the irradiating surface and the vessel surface to be irradiated is maintained to be substantially constant in an irradiation region in which the vessel is irradiated with the electron beam emitted from the irradiating surface.

Embodiment 1

Hereunder, the present invention will be described with reference to an embodiment shown in the accompanying drawings.

Figure 1:
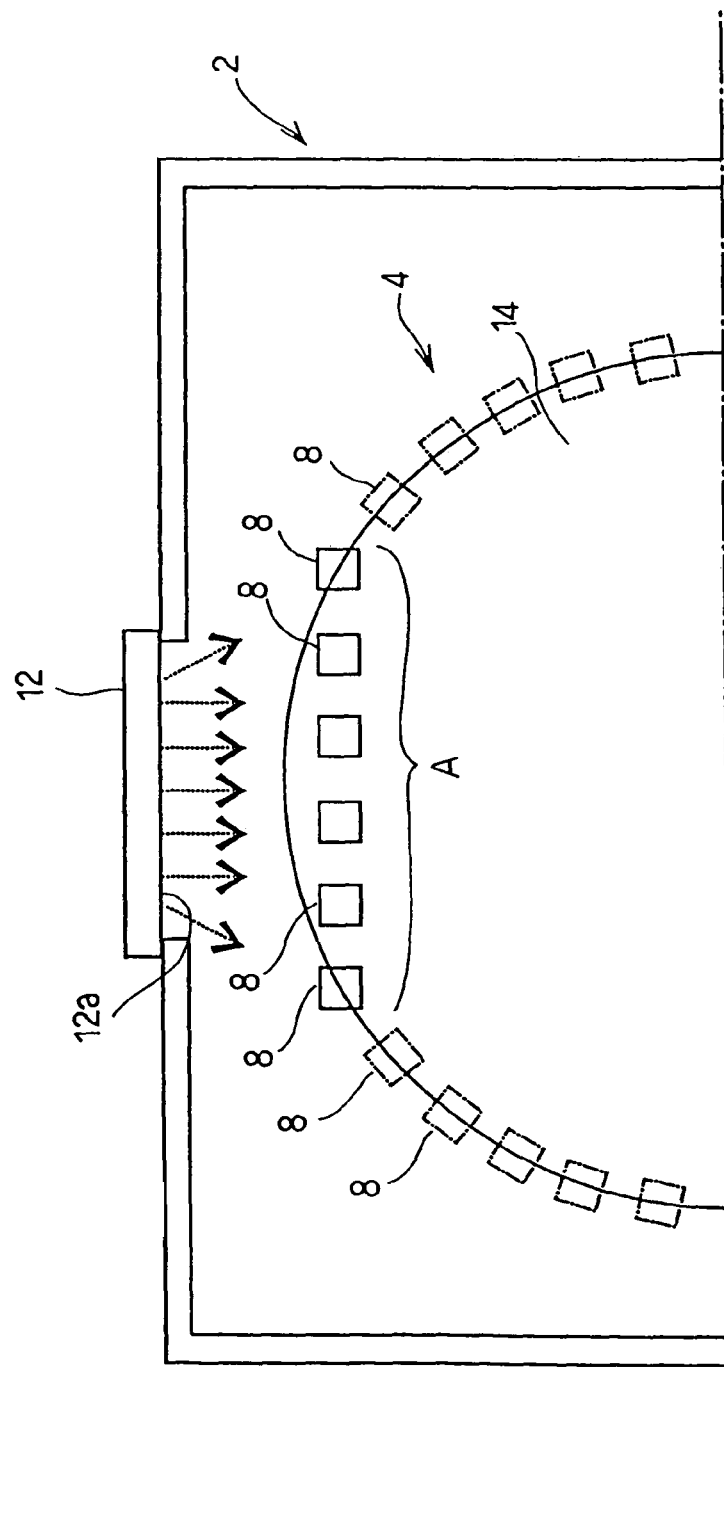
FIG. 1 is a plan view showing an interior (upper half) of a sterilization chamber of a vessel sterilization apparatus (Embodiment 1).
Figure 2:
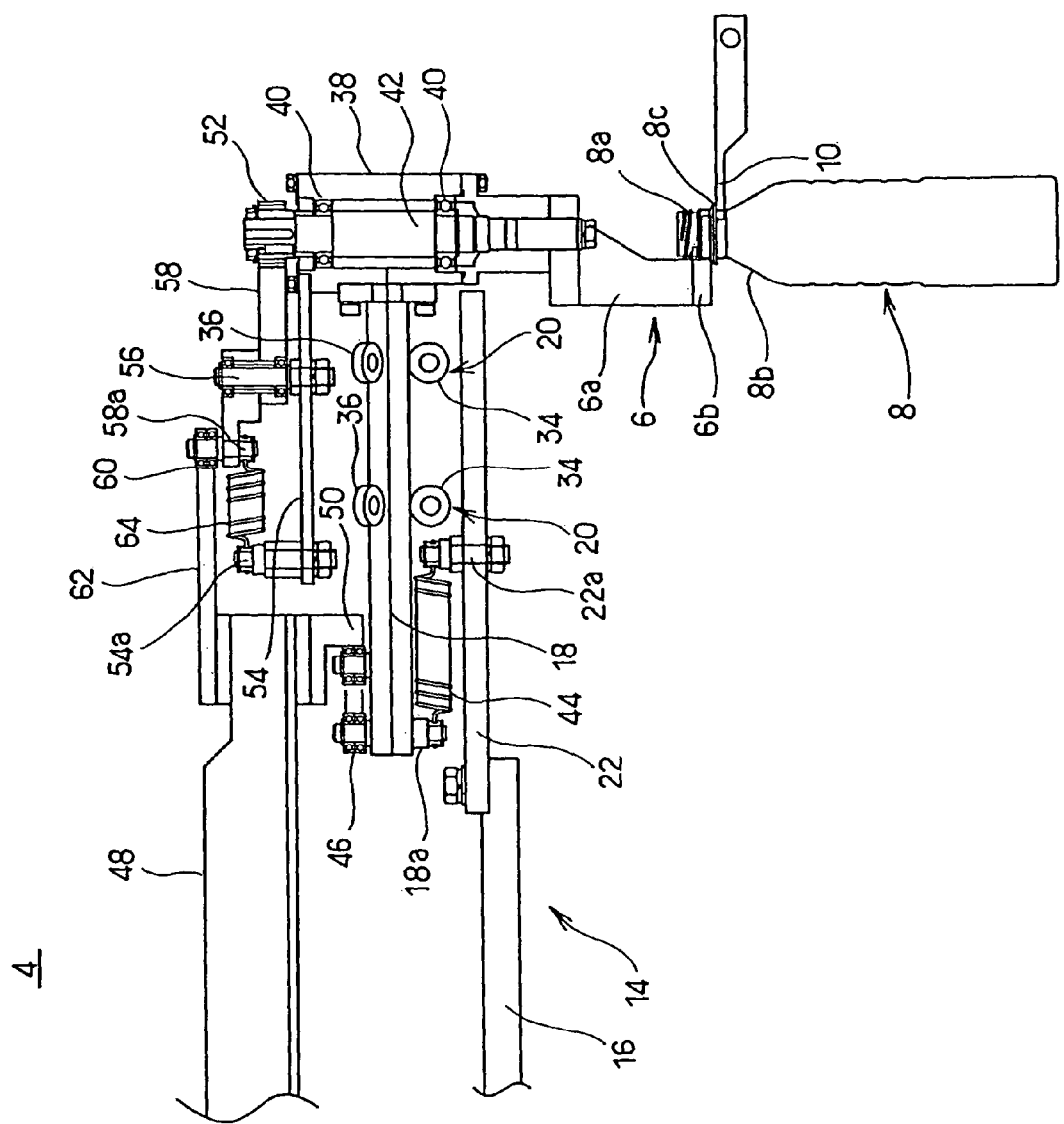
FIG. 2 is an elevational sectional view of an essential portion of a vessel conveying device provided for the vessel sterilization apparatus.

A vessel 8 held by each of the grippers 6 of a vessel conveying device 4 disposed within a sterilization chamber 2 is a bottle formed of a resin material, and as shown in FIG. 2, a flange 8c is formed to a portion on the lower side of a neck portion 8a (i.e., an entire portion, having a smaller diameter, above an inclining shoulder portion 8b of the bottle 8 is called "neck portion 8a"). The gripper 6 grips a portion above the flange 8c of the neck portion 8a of the resin bottle 8. Further, vessel holding means are disposed to an inlet wheel and an outlet wheel (both not shown) arranged respectively on upstream and downstream sides of the vessel conveying device 4, and the vessel holding means 10 act to receive and transfer the resin bottle 8 between the grippers 6 and the vessel holding means 10 in a state each holding a lower side portion of the flange 8c of the neck portion 8a. Further, in this embodiment, there is explained a case where each of the resin bottles 8 having a cross section having substantially square shape (see FIGS. 1 and 3) is conveyed and sterilized. However, it is of course possible to apply bottles such as usual round-shaped bottle or other shaped bottles without being limited to the rectangular resin bottles 8.

The resin bottles 8 to be conveyed in the sterilization chamber 2 are continuously conveyed by an air conveyer, not shown, in which the resin bottles 8 are separated at a predetermined interval by an infeed screw or like and then conveyed into an introduction chamber arranged on the upstream side of the sterilization chamber. Inside the introduction chamber, a rotary-type supply wheel is disposed, and the resin vessels 8 are held by the vessel holding means of the supply wheel, rotated and conveyed, and then transferred to the inlet wheel formed on the inlet side of the sterilization chamber 2, thus being supplied into the sterilization chamber 2. The inlet wheel within the sterilization chamber 2 is provided with the vessel holding means (see FIG. 2) at an equal interval in the circumferential direction thereof, and the resin bottles 8 are conveyed by these vessel holding means 10 with the lower side of the flange 8c of each resin bottle 8 being held.

Each of the resin bottles 8 is transferred to the vessel conveying device 4 from the inlet wheel in the sterilization chamber 2. In this embodiment, the resin bottle 8 held at the lower side of the flange 8c by the vessel holding means 10 of the inlet wheel is held at the upper side than the flange 8c of the neck portion 8a by the gripper 6 of the vessel conveying device 4. The resin bottle 8 held by the gripper 6 of the vessel conveying device 4 is conveyed while being rotated and sterilized by the irradiation with the electron beam, which will be explained hereinafter, and thereafter, is transferred to the vessel holding means 10 on the outlet wheel (not shown) disposed on the downstream side of the vessel conveying device 4. Thereafter, the resin bottle 8 is conveyed while being rotated and discharged from the inside of the sterilization chamber 2 so as to be subjected to the succeeding process. Further, a conveying path, which is not shown, other than the vessel conveying device 4 is one example, and may have a structure other than the one described above.

The sterilization chamber 2 is defined by lead wall sections for shielding the resin bottle 8 from the electron beam or X-ray (braking X-ray) so as not to leak outside at a time when the resin bottle 8 is irradiated with the electron beam for the sterilization thereof. The electron beam irradiator (the entire of which is not shown in figure, but only the irradiating window 12 through which the electron beam is emitted) is disposed on a front surface side (upper side in FIG. 1) of the sterilization chamber 2. The electron beam irradiator emits, as well known, thermal electrons by heating a filament in a vacuum condition inside a vacuum chamber, and the emitted electrons are accelerated by applying high voltage to thereby create high speed electron beam, which is thereafter taken out into atmosphere through a metal window fail such as Ti attached to the irradiating window 12, and the sterilization is performed by irradiating an article to be irradiated (resin bottle 8 in this embodiment) located inside the electron beam irradiation region "A" in front of an opening area of an irradiating surface 12a (that is, a surface on the side of the irradiating window 12 from which the electron beam is emitted is called "irradiating surface 12a").

The rotary-type vessel conveying device 4 according to this embodiment has a characteristic feature in an action of the gripper 6 disposed in the electron bean irradiation region "A" in front of the irradiating surface 12a. Hereunder, the structure of the vessel conveying device provided with the grippers 6 will be explained. The grippers 6 are arranged at the outer peripheral portion of a rotary disc 16 constituting the rotary body 14 at an equal interval between adjacent ones in the circumferential direction thereof. Two guide roller assemblies 20 (see FIGS. 2 and 4) supporting a horizontal rod 18 to which the grippers 6 are mounted so as to be movable forward and rearward. Since the horizontal rod 18 is moved forward and rearward in the irradiating direction of the rotary body 14, the two guide roller assemblies 20, 20 supporting this rod 18 are aligned on a radial line passing the center of the rotary body 14.

Figure 4:
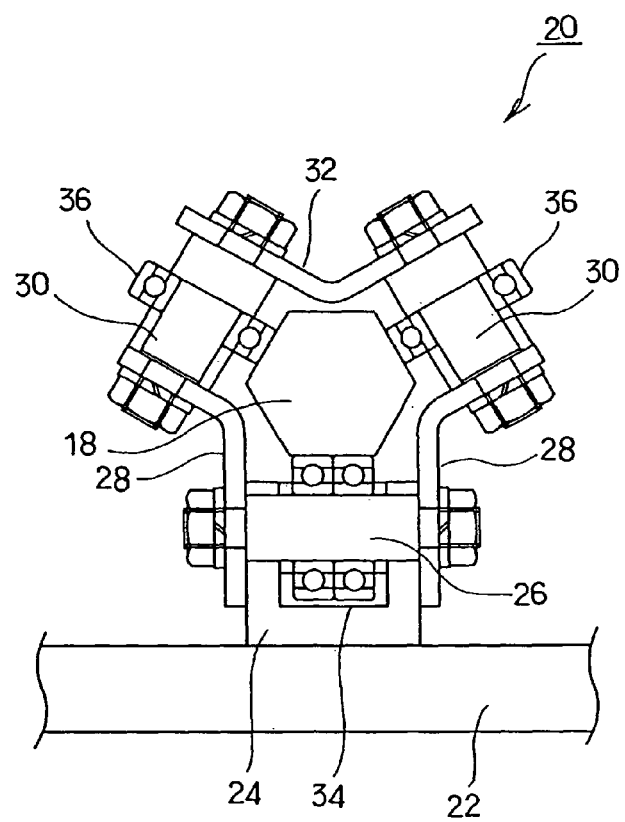
FIG. 4 is an elevational sectional view of a guide roller assembly constituting a portion of the forward/rearward moving means.
Figure 5:
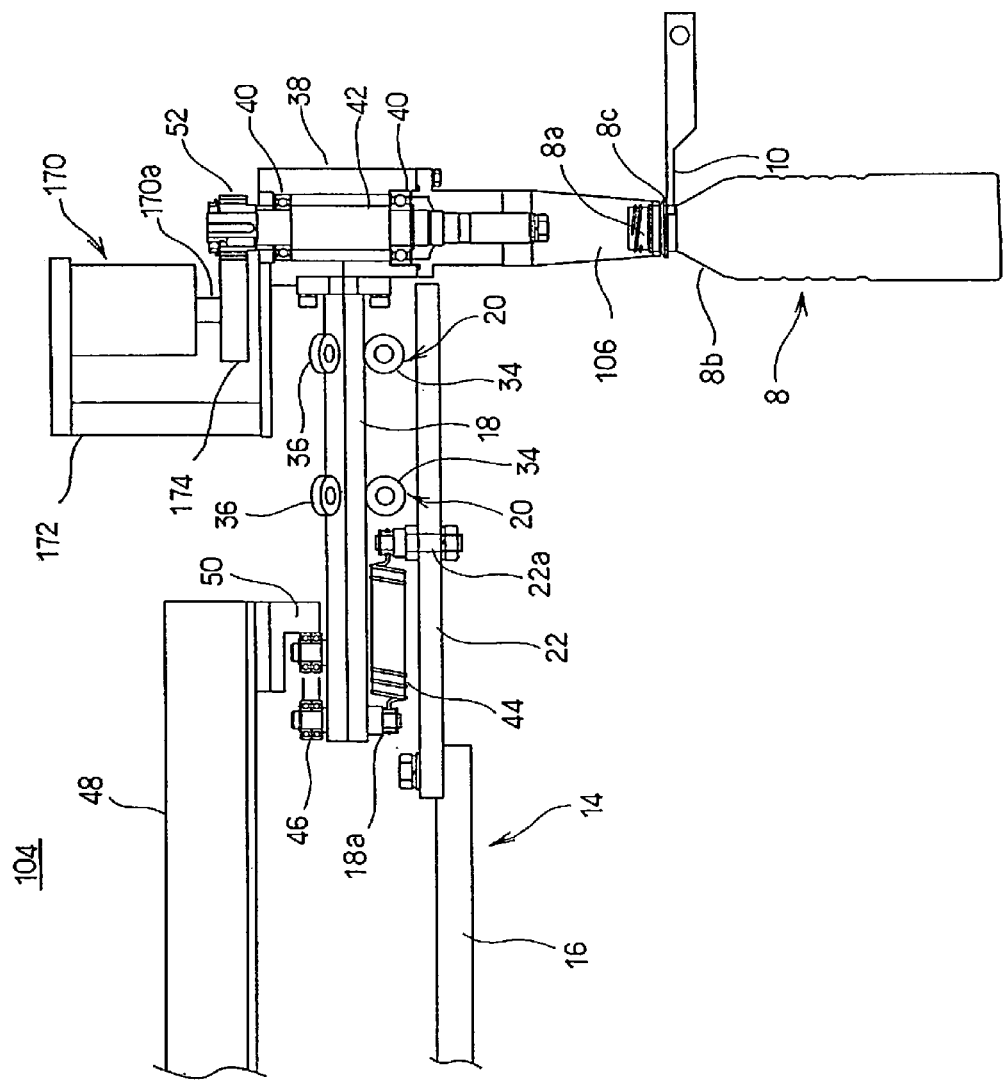
FIG. 5 is an elevational sectional view of an essential portion of a vessel conveying device provided for the vessel sterilization apparatus according to a second embodiment. (Embodiment 2)

The guide roller assemblies 20 are disposed on an annular plate 22 coupled to the outer periphery of the rotary disc 16, and as shown in FIG. 4, and horizontal pins 26 directing in a tangential direction of the rotary body 14 to a base 24 fixed to the annular plate 22. Mount plates 28 are fixed to both end portions of each of the horizontal pins 26 in a manner such that a lower portion of the mount plate 28, which is bent in a L-shape, stands up vertically, and to an upper portion thereof bent in an outward direction, each of inclining pins 30, 30 is fixed such that L-shaped mount plates 32 are connected to the other end portions of both the inclining pins 30, 30. These three pins (one horizontal pin 26 and two inclining pins 30, 30) are arranged at an angle of 60 degrees, and ball bearings (guide rollers) 34, 36, 36 are fitted to the outer peripheral portions of the respective pins 26, 30, 30. Thus, a lower surface of the forward/rearward moving rod 18 having hexagonal section and upper inclining side surfaces are supported by these three guide rollers (horizontal guide roller 34, and the inclining guide rollers 36, 36) so as to be movable forward or rearward in the radial direction.

A cylindrical case 38 is perpendicularly attached to the front end (i.e., end portion on the radially outward direction of the rotary body 14) of the horizontal forward/rearward moving rod 18. A perpendicular rotating shaft 42 is supported to be rotatable through this cylindrical case 38 through ball bearings 40, 40. The gripper 6 is mounted to a lower end portion of the perpendicular shaft 42. Although the details of this gripper 6 is not described herein, gripping members 6b having gripper portions facing each other are attached to lower ends of two plate springs 6a disposed in parallel on both sides of the gripper 6, and when the neck portion 8a of the resin bottle 8 is pushed between the paired gripping members 6b from the front side (right side shown in FIG. 2), the plate springs 6a are widened outward, so that the resin bottle 8 is inserted into both the gripping members 6b. Thereafter, the gripping members 6b are returned by elasticity of both the plate springs 6a and the neck portion 8a of the resin bottle 8 is gripped. In this embodiment, the vessel holding member 10 provided for the inlet wheel, not shown, holds the lower side of the flange 8c of the neck portion 8a of the resin bottle 8 and the gripper 6 grips the upper side of the flange 8c.

A tension spring 44 is disposed between a spring mount portion 18a formed to the loser surface side of a rear end portion of the forward/rearward moving rod 18 (i.e., radially inside portion of the rotary body 14) and a spring mount portion 22a fixed on an annular plate 22 coupled to an outer peripheral portion of the rotary disc 16 to thereby always urge the forward/rearward moving rod 18 toward the radially outward direction of the rotary body 14. Furthermore, a cam follower 46 is mounted on an upper surface side of the rear end portion of the forward/rearward moving rod 18. Further, a forward/rearward moving cam 50 is mounted to an outer peripheral portion on the lower surface side of a fixing side mount plate 48 disposed above the rotary body 14, and the cam follower 46 of the forward/rearward moving rod 18 is pushed by urging force of the tension spring 44. Accordingly, when the rotary body 14 is rotated, the cam follower 46 moves along a cam surface 50a (see FIG. 3) of the forward/rearward moving rod 50, and the horizontal forward/rearward moving rod 18 is moved forward or rearward in accordance with the shape of the forward/rearward moving cam 50.

Figure 3:
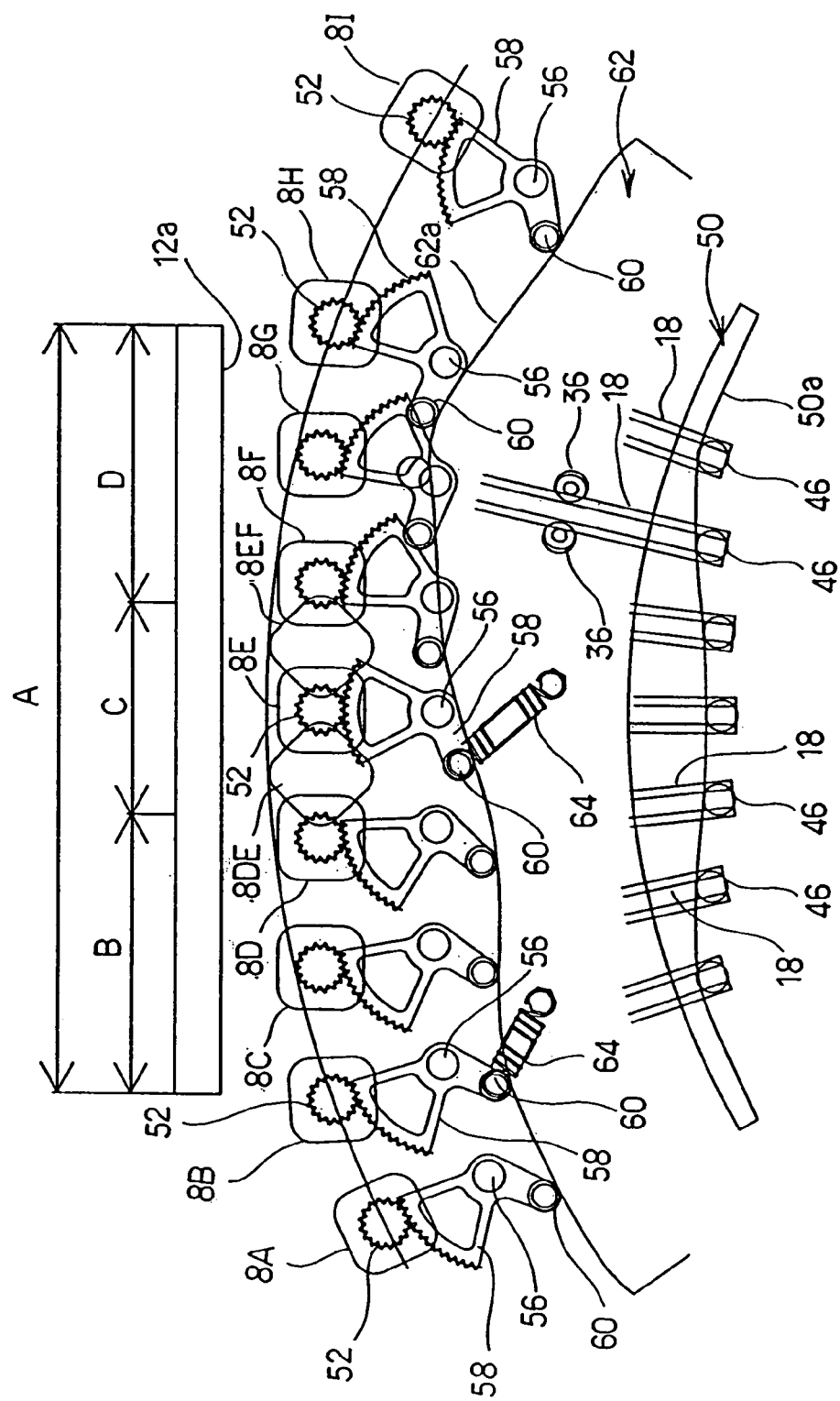
FIG. 3 is a plan view showing a driving portion for a rotating means for rotating the gripper and an forward/rearward moving means for moving forward or rearward the gripper.

In this embodiment, when the rectangular-shaped resin bottle 8 held by the gripper 6 and conveyed as shown in FIG. 3 moves in the electron beam irradiation section "A" on the front side of the irradiating surface 12a of the electron beam irradiator, the forward/rearward moving cam 50 has the cam surface 50a (see FIG. 3) having a shape capable of moving on a straight line approximately in parallel with the irradiating surface 12a.

A pinion gear 52 is fixed to an upper end portion of the perpendicular rotating shaft 42, and a horizontal support plate 54 is fixed to an upper end portion of the cylindrical case 38 fixed perpendicularly to the front end portion of the forward/rearward moving rod 18. A fulcrum pin 56 is fixed on the support plate 54, and an intermediate portion of a segment gear 58 is supported to be rotatable. The segment gear 58 is meshed with the pinion gear 52 of the perpendicular rotating shaft 42. Furthermore, a cam follower 60 is mounted to an upper surface of a rear side end portion of the segment gear 54. Incidentally, a rotational cam 62 is fixed to an upper surface side of the fixing side mount plate 48. According to the structure mentioned above, by the tension spring 64 interposed between the spring mount portion 58a fixed to the lower side of the cam follower 60 and the spring mount portion 54a on the support plate 54, the cam follower 60 attached to the rear end of the segment gear 58 is elastically contacted to the cam surface 62a (FIG. 3) of the rotational cam 62. Accordingly, when the rotary body 14 is rotated, the cam follower 60 is moved along the cam surface 62a of the rotational cam 62, and the segment gear 58 is then rotated in accordance with the shape of the rotational cam 62, and hence, the perpendicular rotating shaft 42 to which the pinion gear 52 and the gripper 6 are mounted are rotated.

In this embodiment, as shown in FIGS. 1 and 3, the rectangular-shaped resin bottles 8 are sterilized, and the shape of the rotational cam 62 is set so as to prescribe the direction of the resin bottle 8 at the time when the resin bottle 8 passes within the electron beam irradiation region "A" in front of the irradiating surface 12a of the electron beam irradiator. In the first area "B" in the electron beam irradiation region "A" in front of the irradiating surface 12a, the pinion gear 52 is rotated such that the rectangular resin bottle 8 is conveyed so that one surface thereof is in parallel with the irradiating surface 12a of the electron beam irradiator. When the resin bottle 8 is conveyed without rotating the gripper 6, a relative angle between the irradiating surface 12a and one surface of the rectangular resin bottle 8 gradually varies in an inclining state (see resin bottle shown in FIG. 3 with letter 8A). However, by rotating the gripper 6 by the rotating means including the segment gear 58, the pinion gear 52, the rotational cam 62 and so on, the resin bottle 8 can be conveyed in a state such that the one surface of the resin bottle 8 maintains the parallel state with respect to the irradiating surface 12a. In the subsequent second area "C", the resin bottle 8 held by the gripper 6 is rotated by approximately 180 degrees. In this second area "C", the rotational cam 62 has a cam-shape such that the segment gear 58 is largely pivoted to thereby rotate the pinion gear 52 by 180 degrees. In the final third area "D", the cam-shape of the rotational cam 62 is designed so that the resin bottle 8 is conveyed in the manner such that a surface reverse to the surface facing to the irradiating surface 12a in the first area "B" is maintained to be in parallel with the irradiating surface 12a. Further, in this embodiment, when the gripper 6 holding the resin bottle 8 in the second area "C" is rotated by 180 degrees, the rotating motion of 180 degrees of the gripper 6 holding the resin bottle 8 may be made twice or third time, or more without limited to only one rotation.

Hereunder, function or operation of the vessel sterilization apparatus of the structure mentioned above will be described.

The resin bottles 8 conveyed from the outside into the sterilization chamber 2 and held by the vessel holding means 10 of the inlet wheel, not shown, are transferred to the grippers 6, respectively, at the transfer-position to the vessel conveying device 4. These grippers 6 are operated to perform the forward/rearward movement and rotational movement, which are mentioned hereinafter, in the electron beam irradiation region "A" positioned in front of the irradiating surface 12a of the electron beam irradiator. However, in regions other than this irradiation region 12, the grippers 6 are moved while directing the resin bottle receiving sides (right side in FIG. 2) of the paired gripping members 6b, 6b to the outer side in the radial direction of the rotary body 14. When each of the grippers 6 reaches the transferring position, the resin bottle 8 which is held at the lower portion of the flange 8c of the neck portion 8a by the vessel holding means 10 is pushed into a space between both the gripping members 6b, 6b. At this time, both the gripping members 6b, 6b are once opened in right and left sides by the elasticity of the plate springs 6a, 6a, and during this moment, the resin bottle 8 is inserted therebetween, and thereafter, the gripping portions 6b, 6b are returned to thereby grip the upper side of the flange 8c of the neck portion 8a of the resin bottle 8.

The gripper 6 holding the resin bottle 8 approaches the electron beam irradiating region "A" by the rotation of the rotary body 14, the cam follower 60 mounted to the rear end of the segment gear 58 meshed with the pinion gear 51 comes into engagement with the cam surface 62a of the rotational cam 62. Subsequently, the cam follower 46 of the horizontal forward/rearward moving rod 18 to which the cylindrical case 38 into which the perpendicular rotating shaft 42, to the lower end portion of which the gripper 6 is mounted, is inserted, is engaged with the cam surface 50a of the forward/rearward moving cam 50.

The cam follower 60 of the segment gear 58 enters the first area "B" of the electron beam irradiation region "A", by the movement of the cam follower 60 on the rotational cam 62, the segment gear 58 is slightly rotated in accordance with the movement of the cam follower 60 on the cam surface 62a, and the pinion gear 52 is then rotated, thereby rotating the gripper 6 fixed to the lower end portion of the rotating shaft 42 to which the pinion gear 52 is mounted, and the resin bottle 8 is moved (see resin bottle shown 8B, 8C, 8D in FIG. 3) in such a manner of maintaining the parallel condition between the electron beam irradiating surface 12a and the surface of the resin bottle 8 facing the irradiating surface 12a.

When the gripper 6 further moves and enters the second area "C" of the irradiation region "A", the segment gear 58 is largely rotated by the change of the shape of the rotational cam 62, and the pinion gear 52 is hence rotated by 180 degrees. In this embodiment, during the movement of the pinion gear 52 from one end to the other end of the segment gear 58 in the engaged condition, the pinion gear 52 rotates substantially by 180 degrees. According to this rotation of the pinion gear 52, the gripper 6 fixed to the lower end portion of the rotating shaft 42 is also rotated by 180 degrees, the surface of the resin bottle 8 directing to the irradiating surface side 12a in the first area "B" (see resin bottle 8 shown with 8D, 8DE, 8E, 8EF, 8F in FIG. 3) is directed to the rear side (i.e., inside in the radial direction of the rotary body 14).

When the gripper 6 further moves and enters the third area "D" of the irradiation region "A", as the rotational cam 62 moves on the cam surface 62a, the segment gear 58 is rotated slightly step by step, and by rotating the pinion gear 52, the gripper 6 fixed to the lower end of the rotating shaft 42 is rotated and the surface of the resin bottle 8 directing the irradiating surface 12a side is moved while maintaining substantially parallel state with the irradiating surface 12a (refer to resin bottle 8 shown with 8F, 8G. 8H in FIG. 3). As mentioned above, by forming the area in which the irradiating surface 12a and the surface of the bottle 8 to be irradiated are opposed to each other in the constant direction at a time when the resin bottle 8 passes in front of the irradiating surface 12a, even if the resin bottle 8 has a rectangular, the resin bottle 8 can be effectively irradiated with the electron beam to thereby sufficiently sterilized.

On the other hand, the cam follower 46 mounted to the rear end portion of the horizontal rod 18 comes into engagement with the cam surface 50a of the forward/rearward moving cam 50. This cam surface 50a has a shape substantially straight in parallel with the irradiating surface 12a in the electron beam irradiation region "A", so that the gripper 6 supported at the front end portion of the horizontal rod 18 is pulled radially inward in accordance with the shape of the cam surface 50a and is moved substantially straightly in parallel with the irradiating surface 12a. In a case where such mechanism for moving the gripper in the forward or rearward direction is not provided, the resin bottle 8 held by the gripper 6 moves so as to describe a circular-arc locus along the outer periphery of the rotary body 14, and hence, since the distance between the resin bottle 8 and the irradiating surface 12a varies in accordance with this movement, which may result in uneven irradiation to the resin bottle 8 with the electron beam. In this viewpoint, however, according to the present embodiment, the resin bottle 8 can be moved with the constant distance being maintained between the resin bottle 8 and the electron beam irradiating surface 12a, and hence, the irradiating dose of the electron beam from the irradiating surface 12a can be made uniform. Further, it is to be noted that the mechanism for moving the gripper 6 forward or rearward is not limited to a sliding mechanism formed from the cam 50, and a mechanism utilizing a link mechanism may be applied. Furthermore, the resin bottle 8 having been subjected to the electron beam irradiation is thereafter discharged from the vessel conveying device 4. However, since the gripper holding the resin bottle 8 is rotated by 180 degrees in the second area "C" of the irradiating region "A", when the resin bottle 8 is discharged, the gripper 6 is again rotated by 180 degrees so as to face the same direction as that in the supply time.

Embodiment 2

In this second embodiment, the shape of a gripper 106 and a structure of rotating means (servo-motor in this embodiment) for rotating the gripper 106 are different from those of the first embodiment, and the other structures are substantially the same, so that different structures are only described and the other structures are omitted in their explanations by applying the same reference numerals.

In the first embodiment, the rotating means for rotating each of the grippers 6 includes the pinion gear 52 fixed to the upper end portion of the perpendicular rotating shaft 42 to which the grippers 6 are mounted, the segment gear 58 to be meshed with the pinion gear 52, the rotational cam 62 for rotating the segment gear 58 and so on. In this second embodiment, however, the gripper 106 is rotated by a servo-motor 170. The servo-motor 170 is mounted, in a downwardly directed fashion, through a bracket 172, to the upper end portion of the cylindrical case 38 fixed to the front end portion of the horizontal rod 18 which moves forward/rearward in the radial direction of the rotary body 14. The servo-motor 170 has a driving shaft 170a to which a drive gear 174 is fixed and is meshed with the pinion gear 52. Further, the forward/rearward moving means (which is composed of the forward/rearward moving cam 50, the cam follower 46, the spring 44, the guide roller assembly 20, and so on) for moving forward or rearward the gripper 106 in the radial direction of the rotary body 14 has the same structure as that of the first embodiment.

Figure 6:
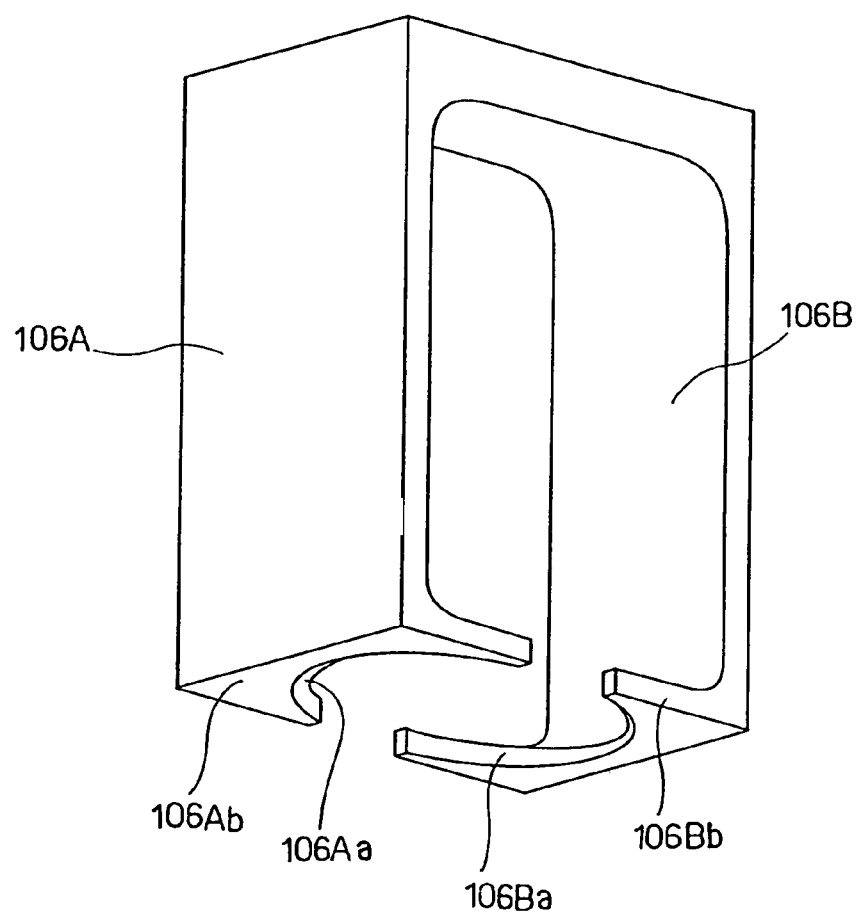
FIG. 6 is a perspective view showing a gripper according to the second embodiment.

The gripper 106 of this embodiment, as shown in FIG. 6, is mounted to the rotating shaft 42 with an opened side of U-shaped frame body being directed downward. The frame body has both leg portions 106A, 106B, and gripping portions 106Ab, 106Bb having circular-arc-shaped holding surfaces 106Aa, 106Ba holding the neck portion 8a of the resin bottle 8 are provided for the lower end portions of these leg portions 106A, 106B. The leg portions 106A, 106B have springy property, and when the neck portion 8a of the resin bottle 8 is pushed between both the gripping portions 106Ab and 106Bb, both the gripping portions 106Ab and 106Bb are opened outward and the neck portion 8a of the resin bottle 8 is inserted therebetween. Thereafter, both the gripping portions 106Ab, 106Bb are returned by the springy elasticity of both the leg portions 106A, 106B to thereby hold the neck portion 8a of the resin bottle 8. Although, in the gripper 6 in the first embodiment, the resin bottle 8 is gotten in or out from one direction, the gripper 106 of this second embodiment has the same shape at its front and rear surface sides (two surfaces opened between both the leg portions 106A, 106B), so that the resin bottle 8 can be gotten into or out from either one of front-side and rear-side directions.

In this embodiment, since the servo-motor 170 is utilized as rotating means for rotating the gripper 106, in accordance with the revolving movement (revolution) of the gripper 106, the resin bottle 8 can be rotated by an optional angle, and as like as in the first embodiment, the irradiating surface 12a of the electron beam irradiator and the surface of the resin bottle 8 to be irradiated with the electron beam can be moved in a state in which both the surfaces are opposed in a constant direction. That is, as far as the resin bottle 8 has a rectangular configuration, the resin bottle 8 can be moved with one surface thereof facing the irradiating surface 12a in parallel therewith. Furthermore, the gripper 6 in the first embodiment has a structure in which the resin bottle 8 is inserted thereinto from one direction, and therefore, if the resin bottle is inverted by 180 degrees in the electron beam irradiating region "A", it is necessary to again rotate the resin bottle 8 by 180 degrees to return the original state for discharging the resin bottle 8 and holding the subsequently conveyed resin bottle 8. However, the gripper 106 according to the second embodiment has the same structures on its front and rear surface sides, so that the resin bottle 8 can be inserted from both the front and rear surface sides, and even if the resin bottle 8 is rotated by 180 degrees, it is not necessary to again return the bottle 8 to original position. That is, in the case where one surface of the resin bottle 8 directing to the irradiating surface 12a in the first area "B" (FIG. 3) in the electron beam irradiation region "A" is inverted in the second area "C" and the other surface reverse to the aforementioned one surface is directed to the irradiating surface 12a, it is not necessary to reversely rotate the resin bottle 8 to return the original position, and the resin bottle 8 can be discharged as it is and the subsequently conveyed resin bottle 8 can be held. Further, it is of course possible to use the gripper 6 as in the first embodiment in this second embodiment in which the servo-motor 170 is used as the rotating means.

The invention claimed is:

1. A vessel sterilization apparatus including a gripper (6) arranged in an outer periphery of a rotary body (14) so as to hold a vessel (8), drive means for rotating the rotary body (14), electron beam irradiating means having a flat electron beam irradiating surface (12a) and irradiating the vessel (8), conveyed with being held by the gripper (6), with the electron beam, and forward/rearward moving means (18, 50) for moving the gripper (6) forward or rearward with respect to the irradiating surface (12a), wherein a distance between the irradiating surface (12a) and the surface of the vessel (8) to be irradiated is maintained to be substantially constant in an irradiation region "A" in which the electron beam is irradiated through the irradiating surface (12a).

2. The vessel sterilization apparatus according to claim 1, wherein the gripper (6) is rotated by substantially 180 degrees in the irradiation region (A).

\* \* \* \* \*